United States Patent
Malpede et al.

(10) Patent No.: US 6,514,485 B1
(45) Date of Patent: Feb. 4, 2003

(54) COMBINATIONS OF SUNSCREENS

(75) Inventors: Alverio Malpede, Bergamo (IT); Giorgio Zanchi, Bergamo (IT)

(73) Assignee: 3V Sigma S.p.A., Milan (IT)

( * ) Notice: Subject to any disclaimer, the term of this patent is extended or adjusted under 35 U.S.C. 154(b) by 0 days.

(21) Appl. No.: 09/475,018

(22) Filed: Dec. 30, 1999

(30) Foreign Application Priority Data

Jan. 11, 1999 (IT) ......................... BG99A0001

(51) Int. Cl.$^7$ ................................. A61K 7/42

(52) U.S. Cl. ......................... 424/59; 424/401

(58) Field of Search ................... 424/401, 59

(56) References Cited

FOREIGN PATENT DOCUMENTS

| EP | 0 570 838 | * 11/1993 |
| EP | 0 832 642 | * 4/1998 |

* cited by examiner

Primary Examiner—Jose' G. Dees
Assistant Examiner—Konata M. George
(74) Attorney, Agent, or Firm—Birch, Stewart, Kolasch & Birch, LLP

(57) ABSTRACT

Combinations of sunscreens comprising at least one specific anti uv-B filter with triazinoaniline structure and at least one specific anti UV-A filter selected from filters with benzoxazol substituted triazinoaniline structure and a long chain alkyl ester of a benzoxazolyl-aminophenyl-cyanoacrylic acid. Cosmetic and dermatological compositions containing them, optionally in combination with vitamins and/or other anti UV-A and anti UV-B filters.

15 Claims, No Drawings

COMBINATIONS OF SUNSCREENS

The present invention relates to combinations of sunscreens comprising at least one anti UV-B filter with triazine structure and at least one anti UV-A filter as defined in the following, and the compositions containing them.

It is well known that sun radiations ranging from 280 to 400 nm are noxious for human skin. Those with a wavelength from 280 to 380 nm, the so-called UV-B radiations, cause erythema and cutaneous sun-burns, whose severity depends on the kind of the skin and on the duration of the exposition to sunlight. Also radiations ranging from 320 to 400 nm, the so called UV-A radiations, which were considered innocuous and only responsible for skin tanning, are, as a matter of fact, harmful, in that they can cause damages to elastine and collagene, with consequent ageing of the skin as well as a number of phototoxic and photoallergic reactions. The damages to DNA structure induced by said radiations are known, as well.

Different combinations of anti UV-A and anti UV-B filters are described in the patent and non-patent literature. Thus, for instance, GB 2 198 944, WO 91/11989 and WO 94/04131 disclose combinations of benzylidenecamphor derivatives or cyanoacrylates (anti UV-B filters) and dibenzoylmethane derivatives (anti UV-A filters), for the purpose of preventing photodegradation of the latter which are known to be poorly stable to light (Int. J. Cosm. Science, 10, 53, 1988). Combinations of anti UV-B filters with triazine structure and dibenzoylmethane derivatives are also described in EP 0 800 813 and EP 0 845 260.

The kind of sunscreens and the amounts at which they are used, alone or in mixtures, are selected depending on the intended protection, as well as on the above mentioned remarks. In particular, an index of this protection is the so-called sun protection factor, (SPF), which is expressed as the ratio of the time of irradiation necessary to reach the erythematogenic threshold in the presence of the UV filter to the time necessary to reach the erythematogenic threshold in the absence of the UV filter.

There is, anyway, a demand for novel, more effective protection systems for those parts of the body which can be damaged by a more or less prolonged exposition to UV radiations, such as skin and hair, which demand is even more felt nowadays in view of the problems deriving from the holes in the ozone layer.

Therefore, the present invention relates to combinations of sunscreens comprising at least one anti UV-B filter selected from the compounds of formulae I and II:

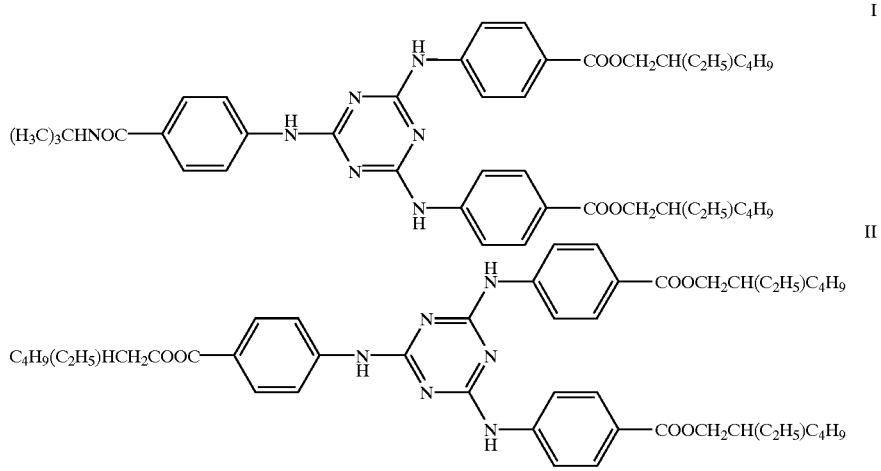

and at least one anti UV-A filter selected from the compounds of formulae III, IV, V, VI and VII:

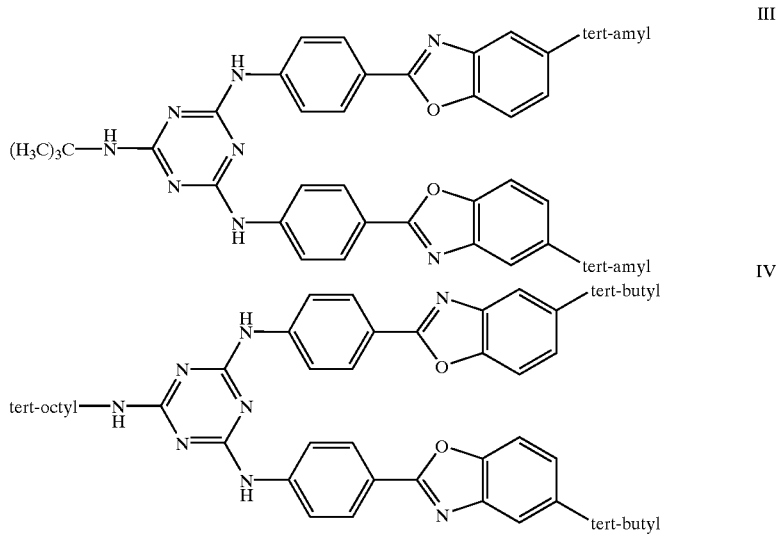

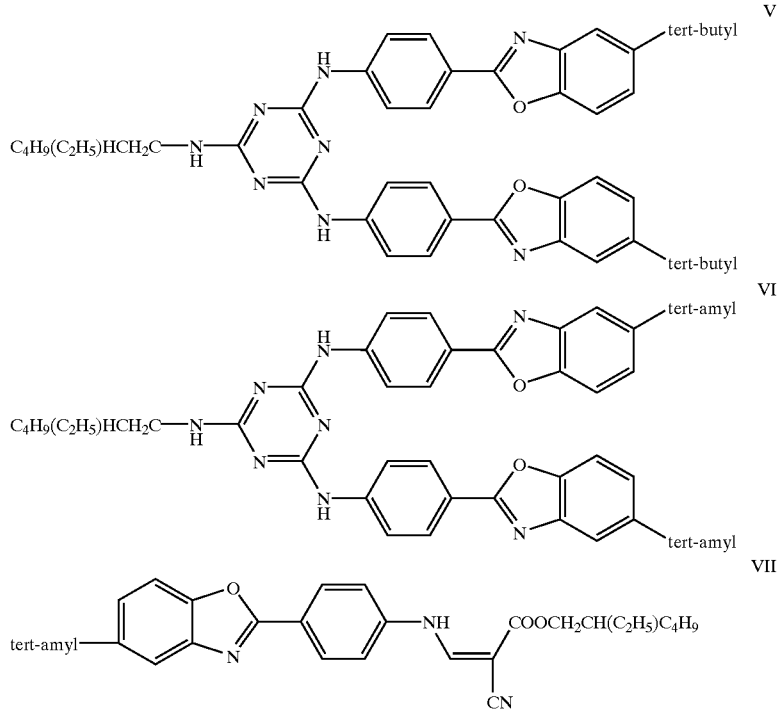

The compounds of formulae I and II are known in literature. Such compounds, as well as the processes for the preparation thereof, are specifically described in EP 0 570 838 and in EP 0 087 098, respectively. The compound of formula IV and the process for the preparation thereof are specifically described in EP 0 832 642, whereas the compounds of formulae III, V and VI are included in the general formula of EP 0 832 642. Finally, the compound of formula VII is included within the general formula of EP 0 832 641. The preparation of the compounds of formulae III, V, VI and VII, carried out according to procedures known in literature, will be reported in the following.

Both EP 0 832 641 and EP 0 832 642 generally claims that the disclosed anti UV-A filters can be combined, in cosmetic compositions, with the anti UV-B filters described in EP 0 570 838. However, nor specific combinations thereof neither cosmetic compositions containing specific combinations of anti UV-A and anti UV-B filters described in the respective EP-A- are specifically reported.

Neither EP 0 832 641 nor EP 0 832 642 disclose that the respective anti UV-A filters can be combined with the compounds of formula II.

Preferred combinations according to the invention comprise at least one anti UV-B filter selected from the compounds of formulae I or II, and at least one anti UV-A filter selected from the compounds of formulae III, IV, V and VI. Most preferred combinations are those comprising, as anti UV-B filter, the compound of formula I, and at least one anti UV-A filter selected from the compounds of formulae III, IV, V and VI.

In the combinations of the present invention, the ratio of the one or more anti UV-A filters to the one or more anti UV-B filters can range within wide limits, for example, it can range from about 0.05 to about 3, preferably from about 0.1 to about 2.

These combinations of sunscreens comprise compounds having a high specific extinction coefficient in the UV region specific for each of them. Moreover, they are resistant to photodegradation induced by sun radiations, and are particularly soluble in the solvents used for the preparation of cosmetic or dermatological compositions.

Therefore, the combinations of sunscreens of the present invention can be used in the protection of human body from the harmful effects of UV radiations, both as they are, dissolved in the suitable solvents, or, preferably, in cosmetic or dermatological compositions.

It has, in fact, surprisingly been found that presence of the anti UV-A filter in the combinations of the invention remarkably enhances the specific extinction in the VU-B region. It is therefore possible to prepare dermatological or cosmetic formulations with SPF (Sun Protection Factor) remarkably higher than that of a corresponding composition containing only the anti UV-B filter, which means that said combinations exert a synergistic effect as far as SPF is concerned.

As mentioned above, the combinations of the invention are particularly resistant to photodegradation induced by sunlight. This feature makes them particularly suitable to the protection of cosmetic compositions whose components can undergo degradation or undesired colour alterations induced by light, such as creams, shampoos, gel, nail lacquers, lotions, perfumes and the like.

On the other hand, such stabilising effect has also been observed when including the above mentioned combinations in photosensitive compositions different from the cosmetic and dermatological ones, such as polymers.

According to the invention, preferred compositions are cosmetic and dermatological compositions, containing said combinations in amounts ranging from about 0.05 to about 30% of the composition total weight: these compositions are a further object of the present invention.

A further object of the present invention is the use of the combinations defined above in the preparation of cosmetic and dermatological compositions for the protection of human skin from sun radiations.

Still a further object of the present invention is the use of the combinations of sunscreens described above for the stabilization of cosmetic and dermatological compositions, and of polymers.

In a preferred embodiment, the cosmetic compositions comprise a combination of sunscreens according to the invention in cosmetically acceptable excipients, such as oil-in-water, water-in-oil, oil-water-oil, water-oil-water, water-in-silicon, oily solutions, lipid fusions, hydroalcoholic, anhydrous or aqueous gels, alcoholic or hydroalcoholic solutions, and analogues. When an oily substance is necessary to dissolve or disperse one or more of the components of the selected combination, this substance is a compound advantageously selected from:

i) hydrocarbons, such as paraffin, mineral oils, and analogs;

ii) oils, butters and natural waxes, such as avocado oil, sunflower oil, almond oil, apricot-stone oil, karite butter, evening primrose oil, black currant oil, borage oil, jojoba oil, safflower oil, wheat germ oil, macadamia oil, rice bran oil, sesame oil, castor oil, coconut oil; unsaponifiable oils of olive, avocado, soya; cocoa butter, bees-wax, candelilla wax, carnauba wax, and analogs;

iii) silicone oils such as dimethicones, cyclomethicones, dimethiconols, alkyldimethicones, and analogs;

iv) esters of straight or branched, saturated or unsaturated aliphatic acids or of aromatic or alkylaromatic acids, having 1 to 25 carbon atoms, said acids being optionally hydroxylated and/or ethoxylated, with mono- or polyhydroxylated aliphatic alcohols, saturated or unsaturated, straight or branched, having 1 to 25 carbon atoms, such as octyldodecyl-neopentanoate, pentaerythritol-dioleate, trimethylolpropan-trioleate, triisostearyl-citrate, diacetin, triacetin, 2-ethyl-hexyl acetate, neopentylglycol oleate, triethylene glycol diacetate, isopropyl myristate, isopropyl palmitate, bis-diglyceryl-caprylate/caprate/isostearate/stearate/hydroxystearate/adipate, dioctyl maleate, di-(2-ethyl-hexyl)malate, ($C_{12-15}$)alkyl benzoates, cetylstearyl octanoate, cetylstearyl isononanoate, 2-ethyl-hexyl palmitate, 2-ethyl-hexyl stearate, $C_{8-10}$ triglycerid, PEG-7 glyceryl coccoate and analogs;

v) amides, such as those mentioned in EP 0,748,623, in particular N,N-diethylmethylbenzamides and ethyl 1-(Nacetyl-N-butyl)-propionate;

vi) ($C_6$–$C_{35}$) alcohols, such as cetyl alcohol, stearyl alcohol, behenyl alcohol, octyldodecyl alcohol, 3,5,5-trimethylhexyl alcohol, 2-butoxyethanol, 2-phenoxyethanol, 2-ethyl-1,3-hexanediol and analogs;

vii) ethers of ($C_8$-$C_{40}$) fatty alcohols, such as di-n-octylether;

viii) butyl ethers of glycols, such as propylene glycol tert-butyl ether, diethylene glycol butyl ether, a (polypropylene glycol)$_{3-53}$ butyl ether, and analogs;

ix) esters of ($C_{1-6}$)alkyl ethers, such as diethylene glycol butyl ether acetate, propylene glycol methylether acetate, and analogs.

For the purposes of the present invention, the substances i) to ix), which are all easily commercially available, can be used either singularly or as mixtures thereof, such as the wax mixtures commercially known under the name CUTINA$^{(R)}$ (Henkel).

Generally, the oily component is used in amounts ranging from about 0.5 to 95% or more of the composition total weight.

A preferred group of oily components are the esters of saturated or unsaturated, straight or branched aliphatic acids, or of aromatic or alkylaromatic acids, having 1 to 25 carbon atoms, said acids being optionally hydroxylated and/or ethoxylated, with mono- or polyhydroxylated aliphatic alcohols, saturated or unsaturated, straight or branched, having 1 to 25 carbon atoms.

Another preferred group of oily components are the N,N-diethyl-methylbenzamides and ethyl 1-(N-acetyl-N-butyl)-propionate.

A third preferred group of oily components are the mixtures of esters of saturated or unsaturated, straight or branched aliphatic acids, or of aromatic or alkylaromatic acids, having 1 to 25 carbon atoms, said acids being optionally hydroxylated and/or ethoxylated, with mono- or polyhydroxylated aliphatic alcohols, saturated or unsaturated, straight or branched, having 1 to 25 carbon atoms, such as N,N-diethyl-methylbenzamides and/or ethyl 1-(N-acetyl-N-butyl)-propionate.

A fourth preferred group of oily components are the silicone oils.

The cosmetic compositions which comprise emulsions, such as those mentioned above, can also include one or more conventional, commercially available emulsifier. These can be anionic emulsifiers, such as soaps of fatty acids with alkali metals (for example, potassium stearate), alkaline-earth metals or aliphatic amines; alkylsulfate salts, such as sodium cetylstearyl sulfate (LANETTE™ E, Henkel); alkylphosphates salts, optionally ethoxylated, such as potassium cethylphosphate (AMPHISOL™ K, Givaudan); condensates of fatty acids with protein hydrolysates (LAMECREME™ LPM, Henkel); mono- and diglycerides anionic esters (GRINDTEK™ CA-P, Grindsted Products Ltd), and analogs. Amphoteric emulsifiers can be used as well, for example phospholipids such as lecithin, or also non ionic emulsifiers. The latter are, for example, ethoxylated compounds of natural oil derivatives, such as hydrogenated castor oil (7)OE (ARLACEL™ 989, ICI); mono- and diglycerides of fatty acids, optionally ethoxylated, such as glyceryl stearate (CUTINA™ GMS, Henkel) and glyceryl (20)OE stearate (CUTINA™ E-24, Henkel); sorbitan ethoxylated esters (TWEEN™, ICI and CRILLET™, Croda) and non-ethoxylated esters (SPAN™, ICI and CRILL™, Croda); polyglycerol esters with fatty acids, such as triglyceryl diisostearate (LAMEFORM™ TGI, Henkel) and triglyceryl distearate (CITHROL™ 2623, Croda); glucose, methylglucose and saccharose esters with ethoxylated and non-ethoxylated fatty acids, such as methylglucose dioleate (GLUCATE™ DO, Amerchol) and methylglucose (20)OE sesquistearate (GLUCAMATE™ SS E-20, Amerchol); ethers of glucose and of its oligomers, optionally esterified with ($C_{10-30}$)aliphatic acids, such as triglycerylmethylglucose distearate (TegoCare™ 450, Goldschmidt) and methyl glucose sesquistearate (TegoCare™ PS, Goldschmidt), or cetylstearyl glucoside (MONTANOV™ 68, Seppic); ethoxylated fatty acids (MYRJ™, ICI); ethoxylated fatty alcohols (BRIJ™, ICI); lanolin and ethoxylated and non-ethoxylated derivatives, such as lanolin (30)OE (AQUALOSE™ L 30. Westbrook); alkylglycols/polyethylene glycols copolymers, such as the copolymer PEG-45/dodecylglycol (ELFACOS™ ST 9, Akzo); silicone emulsifiers (Silicone Fluid 3225 C, Dow Corning; ABIL™ W508 and Th. Goldschmidt AG); fluorinated emulsifiers (FOMBLIN™—Ausimont); polymers of hydroxystearic acid esterified or etherified with polyethylene glycols (PEG), polypropylene glycols (PPG) or copolymers PEG/PPG; and analogs. Instead of these conventional emulsifiers, cross-linked copolymers can also advantageously be used, selected from a) cross-linked copolymers formed by i) acrylic or methacrylic acid, ii) vinyl esters of highly branched trialkylacetic acids of formula VIII

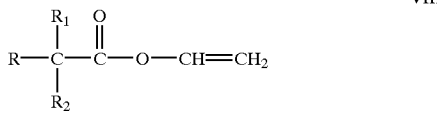

VIII in which R, $R_1$ and $R_2$ are straight alkyl residues, at least one them being methyl, the total sum of the carbon atoms of the acyl residue being preferably 10, and iii) a cross-linking agent such as pentaerythritol triallylether (STABYLEN 30, 3V SIGMA—Bergamo, Italy), and b) cross-linked copolymers formed by i) acrylic or methacrylic acid, ii) acrylates or methacrylates of $(C_{10-30})$aliphatic alkanols, iii) a cross-linking agent like, for instance, the allyl ethers of saccharose or pentaerythritol, as an example, the products known under the trade name PEMULEN™ (B.F. Goodrich).

The amount of emulsifiers which can be used vary from about 0.1 to about 20% of the composition total weight. They can be used singularly or as mixtures thereof.

The cosmetics compositions of the invention can also comprise one or more vitamins, or their precursors, or their analogs. Specifically, the vitamins, or their precursors, or their analogs, which can advantageously be employed are selected from the group consisting of:

i) vitamins of A group, including vitamin $A_2$ and retinal, and their possible esters with straight or branched, saturated or unsaturated $(C_{2-20})$aliphatic monocarboxylic acids or $(C_{3-12})$aliphatic di- or tri-carboxylic acids, said acids being optionally hydroxylated or alkoxylated with PEG, PPG, or copolymers PEG/PPG; or esters with nicotinic acids;

ii) α- and β-carotene;

iii) vitamins of the B group;

iv) vitamin C, and its possible esters with straight or branched, saturated or unsaturated $(C_{2-20})$aliphatic monocarboxylic acids or $(C_{3-12})$aliphatic di- or tricarboxylic acids, said acids being optionally hydroxylated or alkoxylated with PEG, PPG, or copolymers PEG/PPG; or esters with nicotinic acid;

v) the natural and synthetic tocopherols, including Vitamin E, as racemates, or in the form of their possible optically active isomers, and their possible esters with straight or branched, saturated or unsaturated $(C_{2-20})$ aliphatic monocarboxylic acids or $(C_{3-12})$aliphatic di- or tri-carboxylic acids, said acids being optionally hydroxylated or alkoxylated with PEG, PPG, or copolymers PEG/PPG; or esters with nicotinic acid;

vi) Essential Fatty Acids (EFA);

vii) vitamin H;

viii) vitamin P complex; and ix) vitamin PP.

Generally, the amounts of vitamins, or their precursors, or their analogs, which can be employed, can vary within wide limits. Preferably, these amounts are comprised between about 0.02 and about 10% by weight, calculated on the composition total weight.

The cosmetic compositions comprising one or more of the above vitamins represent a further object of the present invention.

Finally, the combinations of sunscreens and the cosmetic compositions of the present invention can also comprise, in combination, one or more anti UV-A or anti UV-B filters selected, for example, from benzylidenecamphor derivatives, dibenzoylmethane derivatives, alkoxycinnamic acid esters and salts, benzophenone derivatives, diphenylcyanoacrylates, salicylic acid derivatives, benzymidazolsulfonic acid derivatives, p-aminobenzoic acid derivatives, 2-(2H-benzotriazol-2-yl)-4-methyl-6-{2-methyl-3-[1,3,3,3-tetramethyl-1-[(trimethylsilyl)oxy]-disiloxanyl]propyl}-phenol(silatrizole), and metal oxides having an atomic number ranging from 21 to 30.

Representative, non limiting, examples, of the sunscreens belonging to the classes of compounds mentioned above are benzylidenecamphor derivatives, such as bicyclo[2.2.1] heptan-2-one 1,7,7-trimethyl-3-[(4-methylphenyl) methylene]; 3-(4'-trimethylammonium)-benzylidenbornan-2-one methylsulfate; and 3,3'-(1,4-phenylenedimethyn)-bis-(7,7-dimethyl-2-oxobicyclo-[2,2,1]-heptane-1-methanesulfonic) acid, )EUSOLEX™ 6300, MEXORIL™ SK and MEXORIL™ SX, respectively); 4-methoxy-4'-tert-butyl-dibenzoylmethane, dibenzoylmethane derivative (PARSOL™ 1789); 2-ethylhexyl-4-methoxycinnamate and 4-methoxycinnamic acid diethanolamine salt, alkoxycinnamic acid derivatives (PARSOL™ MCX and BERNEL™ HYDRO); 2,4-dihydroxybenzophenone, 2-hydroxy-4-methoxy-benzophenone and 5-benzoyl-4-hydroxy-2-methoxy-benzenesulfonic acid, benzophenone derivatives (UVASORB™ 20H, UVASORB™ MET and UVASORB™ S5); 2-ethylhexyl 2-cyano-3,3-diphenylacrylate (UVINUL™ N-539); 2-ethylhexyl 2-hydroxybenzoate, (+)-3,3,5-trimethylcyclohexyl salicylate and salicylic acid triethanolamine salt, salicylic acid derivatives (ESCALOL™ 587, KEMESTER™ HMS and SUNAROME™ W); 2-phenyl-5-benzimidazolyl-sulfonic acid (EUSOLEX™ 232); p-aminobenzoic acid; 2-ethylhexyl 4-dimethylamino-benzoate, ethyl N,N-bis(2-hydroxypropyl)-benzoate and 4-aminobenzoic acid PEG 25, p-aminobenzoic acid derivatives (UVASORB™ DMO, AMERSCREEN™ P and UVINUL™ P25). Among the metal oxides having atomic number ranging from 21 to 30, preferred are titanium dioxide $(TiO_2)$ and zinc oxide (ZnO).

These oxides are preferably used in micronized forms, in which the particles have a size not higher than about 100 nm as for $TiO_2$, and ranging from about 15 and about 300 nm, as for ZnO. These oxides are preferably used in micronized form, in which the particles have a size not higher than about 100 nm as for $TiO_2$, and ranging from about 15 to about 300 nm as for ZnO. Most preferably, the size of the $TiO_2$ particles ranges from about 5 to about 50 nm. Titanium dioxide can have an anatase, rutile or amorphous structure. For the purposes of the invention, these micronized metal oxides can be used either as they are or coated with other agents, such as $Al_2O_3$ or aluminium salts with $C_{10-18}$ aliphatic fatty acids or silicones.

They are easily commercially available products. For example, micronized $TiO_2$ is marketed under the trade name P25 (Degussa), whereas $TiO_2$ coated with aluminium stearate is marketed as MT100T (Tayka Corp.), and that coated with $Al_2O_3$ is known as UFTR (Miyoshi). Micronized ZnO is, in its turn, available as Z-COTE™ (sunSMART) or as SPECTRAVEIL™ (Tioxide).

The cosmetic compositions of the invention can also comprise other conventional components, for example emulsion stabilizers such as sodium chloride or citrate, magnesium sulfate and analogs, in amounts ranging from about 0.1 to about 5% of the composition weight; wetting agents, such as glycerin, propylene glycol or 1,3-butylene glycol, in amounts from about 0.1 to about 30% of the composition weight; thickening agents, such as modified celluloses or acrylic acids polymers or copolymers, in amounts not above 4% of the composition weight; sequestering agents, such as EDTA salts, in amounts not higher than 1% of the composition weight; antioxidizers, such as tocopherols and the esters thereof, hydroxytoluene butoxide or butyl hydroxyanisol, in amounts not above 2% of the composition weight; emollients, such as mineral oils, polysiloxanes, almond oil, vaseline, isopropyl myristate or fatty acids triglycerids, in amounts from about 0.1 to about 95% of the composition weight; moisturizing agents in amounts not above 5% of the composition weight; agents for adjusting pH to the desired values, such as sodium or potassium citrate, sodium or potassium hydroxide, or citric acid monohydrate, in amounts not above 1% of the composition weight; film-forming agents, such as alkylated polyvinilpyrrolidones or high molecular weight waxes, in amounts not above 5% of the composition weight; preservatives, such as 2-bromo-2-nitro-propanediol, sodium dehydro-acetate, isothiazolone, imidazolidinylurea, diazolidinylurea, parabens and hydantoin derivatives (GLYDANT™, Lonza), sorbic acid, benzoic acid and salts thereof, chlorhexidine and the salts thereof, phenoxyethanol, benzyl alcohol and analogs, in amounts not above 10% by composition weight.

Perfumes and dyes can be added according to what known in the art. Moreover, the compositions of the invention can also contain artificial tanning agents such as dihydroxyacetone (DHA) and its derivatives, optionally in the presence of a iron salt, as described in EP-A-0,688,203, in order to provide a less yellowish tan than that given by DHA alone. These artificial tanners can be present in amounts ranging from about 0.1 to about 10% of the composition weight.

The cosmetic compositions of the invention can be prepared according to the procedures known to those skilled in the art. Thus, for example, in the case of compositions in which the cosmetically acceptable carrier is an oil-in-water or water-in-oil emulsion, the two phases should preferably be prepared separately, dissolving or dispersing in any of them the desired components/lipophilic or hydrophilic ingredients, and subsequently mixed.

Examples of said compositions are sun-creams, day creams, moisturizing creams, sun-oils, ointments, lipsticks, solutions, lotions, gels, transparent gels, aerosol, foams and analogs. They contain a selected combination of the present invention together with the other ingredients in the above mentioned weight ratios, as well as any other compatible ingredient conventionally used in cosmetics. Generally speaking, said compositions will comprise a selected combination of the present invention so as to provide an SPF not lower than 2. The combinations of sunscreens of the present invention have often shown a synergistic effect.

The following examples further illustrate the invention. UV spectra were recorded with a Perkin Elmer UV-VIS Lambda II spectrophotometer. The compounds were dissolved in 95% ethanol, at concentrations of 10 mg/l and placed in a 1 cm cell.

EXAMPLE 1

Preparation of the Compound of Formula III

A)—400 ml of acetone cooled to 0° C. are added, under nitrogen stream, with 92.3 g of 2,4,6-trichloro-1,3,5-triazine, then with 38 g of tert-butylamine, always keeping the temperature at about 0° C. After keeping the resulting mixture at this temperature for 30 minutes, 66.7 g of a 30% NaOH aqueous solution, then 400 ml of water are dropped therein, and the resulting mixture is stirred for 1 hour at 0° C. After filtration and washing with water to neutral pH, the resulting precipitate is dried to obtain 108 g of 2-tert-butylamino-4,6-dichloro-1,3,5-triazine. M.p. 129–30° C.

B)—185 Grams of melted p-nitrobenzoyl chloride (80–85° C.) are dropped into a round-bottom flask containing 179 g of 2-amino-4-tert-amyl-phenol in 1000 m of xylene. The resulting suspension is heated slowly to 130° C., neutralizing the formed HCl with aqueous NaOH. When evolution of HCl is over, the reaction mixture is added with 9.5 of p-toluenesulfonic acid, and the whole is heated under reflux for 4 hours. After cooling at 30° C., the precipitate is washed twice with xylene and three times with acetone, then dried in a static dryer, thereby obtaining 228 g of 2-(4-nitrophenyl)-6-tert-amyl-benzoxazole (M.p. 147–48° C.). This product is placed in autoclave containing 1100 ml of ethylene glycol monomethyl ether and 3 g of Pt/C. After washing the reaction medium first with nitrogen and then with hydrogen, the hydrogen pressure is brought to 10 atm, heating to 80–90° C., and these conditions are kept until ceasing of hydrogen adsorption by the system. After cooling and depressurising, the mixture is washed with nitrogen, the catalyst is filtered off and the resulting solution is dried under vacuum. The resulting residue is crystallized from xylene. Yield: 232 g of 2-(4-aminophenyl)-5-tert-amyl-benzoxazole. M.p.: 152–54° C.

C)—11.05 Grams of the compound prepared under A) and 28.56 g of the compound prepared under B) are placed in a round-bottom flask containing 200 ml of xylene. The resulting mixture is refluxed under nitrogen stream for 4 hours, and the formed HCl is neutralized with aqueous NaOH. The xylene phase is recovered, treated with decolourizing earth, then evaporated under vacuum. 34 g of the compound of formula III are obtained. M.p.: 168–69° C., $E_1^1$=1422; λmax=338 nm.

EXAMPLE 2

Preparation of the Compound of Formula V

A)—Operating substantially as described in Example 1A), using 2-ethylhexylamine instead of tert-butylamine, 4,6-dichloro-2-ethylhexylamino-1,3,5-triazine is prepared.

B)—Operating substantially as described in Example 1C), condensing the compound of Example 2A) with the compound of Example 2 of EP 0 832 642, the compound of formula V is obtained. M.p.: 134–36° C. $E_1^1$=1436; λmax=338 nm.

EXAMPLE 3

Preparation of the Compound of Formula VI

A)—Operating substantially as described in Example 1C), condensing the compound of Example 2A) with the compound of Example 1 B), the compound of formula VI is obtained. M.p.: 117–19° C. $E_1^1$=1398; λmax=338 nm.

EXAMPLE 4

Preparation of the Compound of Formula VII

A)—A mixture of 42 grams of the compound of Example 1B) and 30.4 g of ethyl 2-cyano-3-ethoxyacrylate in 250 ml of ethylene glycol is heated slowly to 155–160° C. for three hours, while distilling the formed ethanol. After cooling at 60° C., 300 ml of methanol are added, the mixture is further cooled to 20° C., then filtered and washed with methanol. The filtrate is dried and crystallized from acetone. 47 g of ethyl 3-[4-(5-tert-amyl-2-benzoxazolyl)anilino]-2-cyanoacrylate are obtained.

B)—A mixture of 12.1 g of the compound prepared under A), 90 g of 2-ethylhexanol and 0.4 g of tetrabutylorthotitanate is slowly heated at 160° C. for 3 hours, distilling off the formed ethanol. After distilling off the 2-ethylhexanol excess, a residue is obtained, which is crystallized from n-hexane in the presence of decolourizing earth. 11 g of the compound of formula VII are obtained. M.p.: 95–97° C. $E_1^1$=1309; $\lambda$.max=353 nm.

The following Table shows the specific extinctions of some representative combinations of sunscreens of the invention. Determinations were performed by solubilising equal amounts of the two filters in 95% ethanol, to a final concentration of each filter equivalent to 10 mg/l.

TABLE 1

| Combination (Comp. of formula) | Conc. of the compounds | E1 (nm) | E1 (nm) |
|---|---|---|---|
| I + VI | 10 mg/l + 10 mg/l | 2125 (315) | 1365 (340) |
| I + IV | 10 mg/l + 10 mg/l | 2161 (315) | 1382 (339) |
| I + III | 10 mg/l + 10 mg/l | 2209 (315) | 1437 (339) |

The protective effectiveness of the combinations of the present invention from UV-A and UV-B sun radiations was confirmed by further tests carried out to evaluate the levels of cyclobutanepyrimidine dimers and the expression of protein p53. Cyclobutanepyrimidine dimers are a measure of the damage induced by sun radiation (essentially, the UV-B radiation) which causes a DNA lesion (D. E. Brash et al., Nature, 28, 12, 1982, M. L. Kripke et al. Proc. Natl. Acad. Sci., 89, 7516, 1992); the protein p53, which is expressed by epithelial cells when structural modifications of DNA are induced, as in the case of sun radiations, apparently serves to block cell proliferation to allow DNA restoration before replication (S. Tornaletti et al., Science, 263, 1436, 1994; A. Ziegler et al., Nature, 372, 773; C. Campbell et al., Cancer Res., 53, 2697, 1953; D. P. Lane, Nature, 358, 15).

The tests were carried out substantially following methods known in literature. Small discs of human skin from an healthy donor were used, grown as described by J. J. M. Van de Sandt et al., Toxicology in vitro, 9, 157, 1995. Subsequently, these discs were treated with the combinations of the invention, in amounts of 1 $\mu$l for disc of an oil-in-water emulsion having the following percentage composition by weight:

| | |
|---|---|
| cetearyl polyglucose/cetearyl alcohol | 5.00 |
| cetearyl alcohol | 1.00 |
| dioctyl malate | 1.00 |
| anti UV-B filter | 2.00 |
| anti UV-A filter | 2.00 |
| depurated water | q.s. to 100 |
| imidazolidinyl urea | 0.30 |
| methyl paraben | 0.20 |
| glycerin | 2.00 |
| sodium hydroxide | at pH 6 |

Treatment was carried out 1 hour before exposition to UV radiation. The discs were incubated in humidified incubator at 37° C., 5% $CO_2$, and exposed to filtered radiation from a Xenon lamp of 150 Watt power [filters: long pass 309 (3 mm), WG 305 (5 mm) short pass 400 (3 mm)—Oriel, Stratford, USA]. A dosimeter PMA2100 (Solar Light, Philadelphia, USA) was used equipped with a UV-B sensor biologically weighed (PMA2103) to determinate the dose of biologically effective ultraviolet radiation. Discs previously treated with the combinations of the invention received an amount of radiation of 0.5 MED/min for 24 minutes, i.e. a total radiation amount of 12 MED (MED: Minimum Erythematogenic Dose, DS. Berger, Photochem. Photobiol. 24, 587, 1976). Discs previously incubated as described above were irradiated with a dose of 3 MED. Controls were discs previously incubated as described above, untreated and not irradiated.

The amount of cyclobutanepyrimidine dimers was determined immunohistochemically, substantially according to the procedure described by L. Roza et al., Photochem. Photobiol., 48, 627, 1988; L. Roza et al., Cancer Res., 50. 1905, 1990; L. Roza et al., J. Invest. Derm., 96, 903, 1991. Measurements were made using a CCD Camera (Charged Coupled Device Camera), cooled with liquid nitrogen ($LN_2$ Astromed Ltd., Cambridge, UK).

In representative tests, the mean fluorescence determined on samples of skin treated with the combinations of the present invention, consisting of the compound of formula I and at least one of the anti UV-A filters described above, was found to be up to four times, or more, lower than that determined on samples similarly treated with a control combination consisting of the compound of formula I and compound 4-methoxy-4'-tert-butyl-dibenzoylmethane (PARSOL™ 17989, an anti UV-A filter widely used in the cosmetic compositions), which means a lower formation of cyclobutanepyrimidine dimers and, therefore, of a more effective protection from sun radiations.

The determination of the expression of the protein p53 was performed following substantially the procedure described by G. Krekels et al., Eur. J. Dermatol. 7, 259, 1997. Also in this case the protein p53 was found to be expressed to a much lower extent by the cells of the samples treated with the combinations of the invention used in the above test, compared with the control combination as defined above.

Some representative examples of cosmetic compositions containing the combinations of the invention are reported in the following. The amounts of the single components are expressed as percentages by weight of the composition total weight.

EXAMPLE A

| A face day-cream is prepared from | |
|---|---|
| 1. Cetylstearyl glucoside | 4.00 |
| 2. Glyceryl stearate | 1.00 |
| 3. Cetylstearyl alcohol | 1.00 |
| 4. $C_{12-15}$ alkylbenzoate | 5.00 |
| 5. Octyl octanoate | 5.00 |
| 6. Dimethicone | 0.50 |
| 7. Compound of formula I | 1.00 |
| 8. Compound of formula IV | 1.00 |
| 9. Depurated water | q.s. to 100 |
| 10. Imidazolidinyl urea | 0.30 |
| 11. Methyl p-hydroxybenzoate | 0.20 |
| 12. Glycerin | 3.00 |
| 13. Perfume | 0.30 |

The mixture of components 1 to 6 is melted and heated to 70° C., then components 7 and 8 are added, under strong stirring (phase A). Separately, water is heated to 70° C. (phase B). Phase A is added to phase B in a turboemulsifier. The mixture is cooled to room temperature, then glycerin, preservatives and perfume are added.

EXAMPLE B

| A fluid oil-in-water emulsion is prepared from | |
|---|---|
| 1. Sorbitan(20)OE stearate | 0.25 |
| 2. Avocado Oil | 3.00 |
| 3. Octyl palmitate | 3.00 |
| 4. Mineral oil | 3.00 |
| 5. Compound of formula I | 3.00 |
| 6. Compound of formula VI | 2.00 |
| 7. Depurated water | q.s. to 100 |
| 8. Stabylen 30 (polymeric emulsifier 3V SIGMA, Bergamo, Italy) | 0.25 |
| 9. Sodium hydroxide | q.s. to pH 7 |
| 10. Diazolidinyl urea | 0.30 |
| 11. Isothiazolone | 0.05 |
| 12. Propylene glycol | 3.00 |

The mixture of components 1 to 4 is heated to 60° C. then components 5 and 6 are added (phase A). Separately, component 8 is dispersed in water, at 60° C., under stirring (phase B). Subsequently, phase A is added to phase B in a in turboemulsifier, and pH is adjusted to 7 with sodium hydroxide. The mixture is cooled to room temperature, then propylene glycol, preservatives and perfume are added.

EXAMPLE C

| An anhydrous ointment is prepared from | |
|---|---|
| 1. Mineral oil | q.s. to 100 |
| 2. Cetylstearyl isononanoate | 30.00 |
| 3. $C_{8-10}$ triglycerid | 30.00 |
| 4. Compound of formula I | 5.00 |
| 5. Compound of formula IV | 1.00 |
| 6. Titanium dioxide micronized | 2.00 |
| 7. Hydrogenated castor oil | 1.50 |
| 8. Pyrogenic silica | 1.50 |
| 9. Perfume | 0.30 |

The mixture of components 1, 2 and 3 is heated to 60° C. and components 4 and 5 are added, under stirring. Components 6, 7 and 8 are then dispersed in the above mixture, under strong stirring. The mixture is finally cooled to room temperature and added with the perfume.

EXAMPLE D

| A fluid water-in-oil emulsion is prepared from | |
|---|---|
| 1. Hydrogenated castor oil (7) OE | 7.50 |
| 2. Lanolin alcohols in mineral oil | 2.50 |
| 3. Hydrogenated polyisobutene | 5.00 |
| 4. Octyl octanoate | 5.00 |
| 5. $C_{8-10}$ triglycerid | 3.00 |
| 6. Compound of formula I | 5.00 |
| 7. Compound of formula VI | 2.00 |
| 8. 4-methoxy-4'-tert-butyl-dibenzoylmethane (PARSOL ™ 1789) | 2.00 |
| 9. Depurated water | q.s. to 100 |
| 10. Dimethyl-dimethylol-hydantoin | 0.30 |
| 11. Phenoxyethanol and parabens | 1.00 |
| 12. Glycerin | 5.00 |
| 13. Perfume | 0.30 |

The mixture of components 1 to 5 is heated to 70° C. and components 6, 7 and 8 are added, under stirring (phase A). Separately, water is heated to 70° C. and added to phase A in a turboemulsifier. The mixture is cooled to room temperature, added with the preservatives mixed in glycerin and with the perfume.

EXAMPLE E

| A high-protection water-in-oil cream is prepared from | |
|---|---|
| 1. Triglyceryl diisostearate | 4.00 |
| 2. Beeswax | 2.00 |
| 3. Mineral oil | 10.00 |
| 4. Octyl octanoate | 5.00 |
| 5. Cyclomethicone | 5.00 |
| 6. Compound of formula I | 5.00 |
| 7. Compound of formula VI | 5.00 |
| 8. Hydrogenated castor oil | 0.50 |
| 9. Depurated water | q.s. to 100 |
| 10. Sodium dehydroacetate | 0.30 |
| 11. Phenoxyethanol and parabens | 1.00 |
| 12. Glycerin | 5.00 |
| 13. Perfume | 0.30 |

The mixture of components 1 to 5 is melted at 60° C. and components 6 and 7 are added (phase A). Component 8 is subsequently dispersed in this phase in a turboemulsifier. Separately, water is heated to 60° C. and added to phase A in a turboemulsifier. The mixture is cooled to room temperature, added with the preservatives, glycerin and the perfume.

EXAMPLE F

| A cream oil-in-water is prepared from | |
|---|---|
| 1. Cetylstearyl alcohol (33) OE | 2.50 |
| 2. Glyceryl stearate (20) OE | 2.00 |
| 3. Behenyl alcohol | 2.00 |
| 4. Isohexadecane | 10.00 |
| 5. Safflower oil | 3.00 |
| 6. Borage oil | 2.00 |
| 7. Butyl hydtoxyanisol | 0.10 |
| 8. Copolymer PVP/eicosene | 1.00 |
| 9. Compound of formula I | 3.00 |
| 10. Compound of formula VI | 2.00 |
| 11. EUSOLEX ™ 6300 | 1.00 |
| 12. Micronized zinc oxide | 2.00 |
| 13. Depurated water | q.s. to 100 |
| 14. SYNTHALEN ™ K (Carbomer 940 - 3V SIGMA, Bergamo, Italy) | 0.10 |
| 15. Aminomethyl propanol | 0.10 |
| 16. Imidazolidinyl urea | 0.30 |
| 17. Phenoxyethanol and parabens | 1.00 |
| 18. Butylene glycol | 2.00 |
| 19. Perfume | 0.30 |

The mixture of components 1 to 8 is melted at 70° C. and components 9 to 12 are added, under strong stirring (phase A). Separately, component 14 is dispersed in water at 70° C., under stirring (phase B). Phase A is then added to phase B in a turboemulsifier, and the resulting mixture is then neutralized (pH 7) with component 15. Finally, the mixture is cooled to room temperature and added with preservatives, butylene glycol and perfume.

EXAMPLE G

| A sun-oil is prepared from | |
|---|---|
| 1. Dioctyl cyclohexane | q.b. 100 |
| 2. C$_{8-10}$ triglycerid | 20.00 |
| 3. Isopropyl palmitate | 30.00 |
| 4. Cyclomethicone | 10.00 |
| 5. Perfume | 0.30 |
| 6. Compound of formula I | 3.00 |
| 7. Compound of formula VI | 2.00 |

The mixture of components 1, 2 and 3 is added, under stirring, with components 6 and 7. The resulting mixture is heated to dissolution of components 6 and 7, then cooled to room temperature; finally, components 4 and 5 are added.

EXAMPLE H

| An oil-in-water milk is prepared with | |
|---|---|
| 1. PEG-4 Polyglyceryl 2-laurate | 2.00 |
| 2. Dicaprylyl ether | 7.50 |
| 3. Propylene glycol dicaprylate/dicaprate | 9.50 |
| 4. Cetyl lactate | 3.00 |
| 5. Cetylstearyl alcohol | 0.75 |
| 6. Dimethicone | 0.50 |
| 7. Compound of formula I | 4.00 |
| 8. Compound of formula VI | 2.00 |
| 9. Depurated water | q.s. to 100 |
| 10. Stabylen 30 (3V SIGMA, Bergamo, Italy) | 0.25 |
| 11. Trilauryl 40E phosphate | 0.80 |
| 12. Aminomethyl propanol | 0.20 |
| 13. Butylene glycol | 2.00 |
| 14. Phenoxyethanol and parabens | 1.00 |
| 15. EDTA disodium | 0.05 |
| 16. Perfume | 0.30 |

The mixture of components 1 to 6 is heated at 70° C. and, under stirring, is added with components 7 and 8 (phase A). Separately, compound 10 is dispersed into water, previously heated to 70° C., and the resulting dispersion is added with component 11 (phase B). Then phase A is added to phase B in a turboemulsifier, the obtained mixture is cooled to room temperature, subsequently neutralized with component 12 and finally added with components 13 to 16.

EXAMPLE J

| An oil-in-water cream is prepared with | |
|---|---|
| 1. PEG-110 stearate | 2.00 |
| 2. Glyceryl stearate | 1.00 |
| 3. Cetearyl alcohol | 2.50 |
| 4. Stearic acid | 5.00 |
| 5. Propylene glycol dicaprylate/dicaprate | 9.50 |
| 6. C$_{18-36}$ acids glycolic esters | 2.00 |
| 7. α-tocopheryl acetate | 1.00 |
| 8. Compound of formula I | 4.00 |
| 9. Compound of formula VI | 4.00 |
| 10. Isohexadecane | 5.00 |
| 11. Cyclomethicone | 2.50 |
| 12. Depurated water | q.s. to 100 |
| 13. Potassium cethylphoshate | 0.50 |
| 14. PNC 30 (3V SIGMA, Bergamo, Italy) | 0.15 |
| 15. Butylene glycol | 1.50 |
| 16. Green tea extract | 1.00 |
| 17. Imidazolidinyl urea | 0.30 |

-continued

| An oil-in-water cream is prepared with | |
|---|---|
| 18. Methyl paraben | 0.20 |
| 19. Propyl paraben | 0.10 |
| 20. Perfume | 0.30 |
| 21. Retinyl palmitate | 1.00 |

The mixture of components 1 to 7 is heated to 70° C., and subsequently added with components 8 and 9 (phase A). Subsequently components 10 and 11 are added. Component 14 is dispersed in water previously heated to 70° C., and the resulting dispersion is added with component 13 (phase B). Phase a is added to phase b in a turboemulsifier; the resulting mixture is then cooled at room temperature and components 15 to 21 are subsequently added.

What is claimed is:

1. A combination of sunscreens comprising as an anti UV-B filter the compound 4,6-bis-[4-(2-ethylhexyloxycarbonyl)anilino]-2-[4-(tertbutylaminocarbonyl)anilino]-1,3,5-triazine and as an anti UV-A filter the compound, 4,6-bis-[4-(5-tert-butyl-benzoxazol-2-yl)anilino]-2-(2-ethylhexylamino)-1,3,5-triazine wherein the ratio of the anti UV-A filter to the anti UV-B filter ranges from about 0.05 to about 3.

2. A combination of sunscreens comprising as an anti UV-B filter the compound 4,6-bis-[4-(2-ethylhexyloxycarbonyl)anilino]-2-[4-(tert-butylaminocarbonyl)anilino]-1,3,5-triazine and as an anti UV-A filter the compound, 4,6-bis-[4-(5-tert-amyl-benzoxazol-2-yl)anilino]-2-(2-ethylhexylamino)-1,3,5-triazine wherein the ratio of the anti UV-A filter to the anti UV-B filter ranges from about 0.05 to about 3.

3. Combinations as claimed in claim 1 or claim 2, in which the ratio of the specified anti UV-A filters to the specified anti UV-B filter ranges from about 0.1 to about 2.

4. Cosmetic and dermatological compositions containing a combination as claimed in claim 1 or claim 2, in amounts ranging from about 0.05 to about 30% of the total weight of the composition.

5. Cosmetic compositions as claimed in claim 4, which are oil-in-water emulsions, water-in-oil emulsions, oil-water-oil emulsions, water-oil-water emulsions, water-in-silicone emulsions, oily solutions, lipid fusions, hydro-alcoholic gels, anhydrous gels, aqueous gels, alcoholic solutions, or hydro-alcoholic solutions.

6. Cosmetic compositions as claimed in claim 4, in which a solvent or dispersant of the oily phase is selected from hydrocarbons; oil, butters and natural waxes; silicone oils; esters of straight or branched, saturated or unsaturated aliphatic acids or esters of aromatic or alkylaromatic acids, having 1 to 25 carbon atoms, said acids being optionally hydroxylated and/or ethoxylated, with mono- or polyhydroxylated aliphatic alcohols, saturated or unsaturated, straight or branched, having 1 to 25 carbon atoms; amides; alcohols containing 6 to 35 carbon atoms; ethers of fatty alcohols having 8 to 40 carbon atoms; butyl ethers of glycols or esters of ($C_{1-6}$)alkyl ethers.

7. Cosmetic compositions as claimed in claim 4, in which a solvent or dispersant of the oily phase is selected from esters of straight or branched, saturated or unsaturated aliphatic acids or esters of aromatic or alkylaromatic acids, having 1 to 25 carbon atoms, said acids being optionally hydroxylated and/or ethoxylated, with mono- or polyhydroxylated aliphatic alcohols, saturated or unsaturated, straight or branched, having 1 to 25 carbon atoms, N,N- diethyl-methyl-benzamides or ethyl 1-(N-acetyl-N-butyl) propionate, or mixtures thereof.

8. Cosmetic compositions as claimed in claim 4, in which a solvent or dispersant of the oily phase is a silicone oil.

9. Cosmetic compositions as claimed in claim 4, in which a solvent or dispersant of the oily phase is used in amounts ranging from about 0.5 to about 95% of the total weight of the composition.

10. Compositions as claimed in claim 4, comprising vitamins, or vitamin precursors, or vitamin analogs, selected from the group consisting of:
   i) vitamins of the A group, including vitamin A2 and retinal, and their possible esters with straight or branched, saturated or unsaturated ($C_{2-20}$)aliphatic monocarboxylic acids or ($C_{3-12}$)aliphatic di- or tri-carboxylic acids, said acids being optionally hydroxylated or alkoxylated with PEG, PPG, or copolymers PEG/PPG; or esters with nicotinic acid;
   ii) α- and β-carotene;
   iii) vitamins of the B group;
   iv) vitamin C, and its possible esters with straight or branched, saturated or unsaturated ($C_{2-20}$)aliphatic monocarboxylic acids or ($C_{3-12}$)aliphatic di- or tri-carboxylic acids, said acids being optionally hydroxylated or alkoxylated with PEG, PPG, or copolymers PEG/PPG; or esters with nicotinic acid;
   v) the natural and synthetic tocopherols, as racemates or in the form of their possible optically active isomers, and their possible esters with straight or branched, saturated or unsaturated ($C_{2-20}$)aliphatic monocarboxylic acids or ($C_{3-12}$)aliphatic di- or tri-carboxylic acids, said acids being optionally hydroxylated or alkoxylated with PEG, PPG, or copolymers PEG/PPG; or esters with nicotinic acid;
   vi) Essential Fatty Acids (EFA);
   vii) Vitamin H;
   viii) vitamin P complex; and
   ix) vitamin PP.

11. Compositions as claimed in claim 4, in which the vitamins, or their precursors, or their analogs, are used in amounts ranging from about 0.02 to about 10% by weight of the total weight of the composition.

12. Compositions as claimed in claim 4, comprising one or more additional anti UV-A or anti UV-B filters selected from benzylidenecamphor derivatives, dibenzoylmethane derivatives, alkoxycinnamic acid esters and salts, benzophenone derivatives, diphenylcyanoacrylates, salicylic acid derivatives, benzimidazolsulfonic acid derivatives, p-aminobenzoic acid derivatives, 2-(2H-benzotriazol-2-yl)-4-methyl-6-{2-methyl-3-[1,3,3,3-tetramethyl-1-[(trimethylsilyl)oxyl]-disiloxanyl]-propyl}-phenol, and oxides of metals having an atomic number ranging from 21 to 30.

13. Compositions as claimed in claim 4, having a sun protecting factor (SPF) not lower than 2.

14. A method for preparing a dermatological or cosmetic composition useful for protecting human skin from sun radiation, comprising the step of adding to the composition a sun screening effective amount of a combination of claim 1 or of claim 2.

15. A method for preparing a dermatological or cosmetic composition or polymer, comprising the step of adding to a composition or polymer a stabilization effective amount of a combination of claim 1 or of claim 2.

* * * * *